United States Patent [19]

Suami

[11] 4,129,719
[45] Dec. 12, 1978

[54] 5,6-EPINEAMINE AND PROCESS FOR PREPARING THE SAME

[76] Inventor: Tetsuo Suami, No. 5-8, Naka-machi 3-chome, Musashina-shi, Tokyo, Japan

[21] Appl. No.: 799,011

[22] Filed: May 20, 1977

[30] Foreign Application Priority Data

May 28, 1976 [JP] Japan .................................. 51-61246

[51] Int. Cl.$^2$ ............................................ C07H 3/10
[52] U.S. Cl. ...................................... 536/17; 424/180; 536/4; 536/18
[58] Field of Search ................................ 536/4, 17, 18

[56] References Cited

U.S. PATENT DOCUMENTS 3,963,695  6/1976  Cooper et al. ........................ 536/17

Primary Examiner—Johnnie R. Brown
Attorney, Agent, or Firm—Sughrue, Rothwell, Mion, Zinn and Macpeak

[57] ABSTRACT

5,6-Epineamine represented by the formula (I)

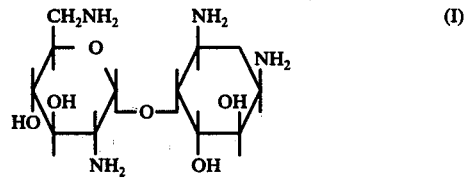

and a process for preparing 5,6-epineamine of the formula (I) above which comprises hydrolyzing the epoxy group of a compound of the formula (II)

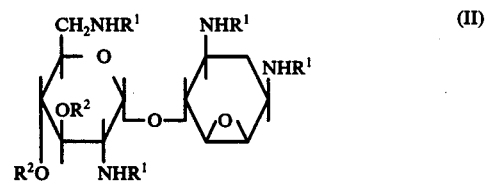

wherein $R^1$ represents a protective group for an amino group and $R^2$ represents a protective group for a hydroxyl group, and removing the protective groups for the amino and hydroxyl groups.

2 Claims, No Drawings

5,6-EPINEAMINE AND PROCESS FOR PREPARING THE SAME

BACKGROUND OF THE INVENTION

1. Field of the Invention

This invention relates to 5,6-epineamine having an antibiotic effect against various pathogenic bacteria including antibiotic-resistant microorganisms, and a process for preparing the same.

2. Description of the Prior Art

It is well known that certain neamine derivatives exhibit antimicrobial activities against various antibiotic-resistant microorganisms as reported in *J. Antibiotics,* 24(10) 711, (1971).

Investigations have been made on aminocyclitol derivatives having antimicrobial activities on antibiotic-resistant microorganisms and it has been found that neamine having a deoxy structure in the deoxystreptamine moiety is also effective against antibiotic-resistant microorganisms.

Also, it has been found that 5-deoxyneamine and 6-deoxyneamine have excellent antimicrobial activities, as disclosed in U.S. patent application Ser. No. 730,396, filed Oct. 7, 1976 now U.S. Pat. No. 4,103,082.

SUMMARY OF THE INVENTION

An object of the present invention is to provide 5,6-epineamine of the formula (I)

$$\text{(I)}$$

which has antimicrobial activities against various pathogenic bacteria including antibiotic-resistant microorganisms and which is useful as an intermediate for synthesizing various novel antibiotics.

Another object of the present invention is to provide a process for preparing 5,6-epineamine of the formula $$\text{(I)}$$

which comprises hydrolyzing the epoxy group of a compound of the formula (II)

$$\text{(II)}$$

wherein $R^1$ represents a protective group for an amino group and $R^2$ represents a protective group for a hydroxyl group, and removing the protective groups for the amino and hydroxyl groups.

DETAILED DESCRIPTION OF THE INVENTION

Extensive investigations to synthesize various sugar compounds have now been conducted and, as a result, it has been found that 5,6-epineamine represented by the formula (I) above exhibits antimicrobial activities against various pathogenic bacteria including antibiotic-resistant microorganisms, and that 5,6-epineamine of the formula (I) is also useful as an intermediate for synthesizing various novel antibiotics.

In accordance with the present invention, 5,6-epineamine of the formula (I) can be prepared by hydrolyzing the epoxy group of a compound represented by the formula (II).

$$\text{(I)}$$

wherein $R^1$ represents a protective group for an amino group and $R^2$ represents a protective group for a hydroxyl group.

Preferred examples of the compound of the formula (II) are those in which $R^1$ is a group such as an alkoxycarbonyl group, particularly an alkoxycarbonyl group having 1 to 4 carbon atoms in the alkoxy moiety thereof, e.g., a methoxycarbonyl group, an ethoxycarbonyl group, an isopropoxycarbonyl group and a butoxycarbonyl group; an aryloxycarbonyl group, e.g., having 7 to 10 carbon atoms such as a phenoxycarbonyl group and a p-nitrophenoxycarbonyl group; an aralkoxycarbonyl group, e.g., having 8 to 10 carbon atoms such as a benzyloxycarbonyl group, a p-methoxybenzyloxycarbonyl group, a p-ethoxybenzyloxycarbonyl group, a p-chlorobenzyloxycarbonyl group and a p-nitrobenzyloxycarbonyl group, and those in which $R^2$ is a group such as an acyl group, e.g., having 2 to 5 carbon atoms such as an acetyl group, a propionyl group and a butyryl group; an aroyl group, e.g., having 7 to 10 carbon atoms such as a benzoyl group, a p-chlorobenzoyl group and a p-nitrobenzoyl group; a R'-CH(OR'')- group and a R'-CR''(OR''')- group wherein R', R'' and R''' may be the same or different and represent a hydrocarbon chain and R' and R'' may join to form a hydrocarbon ring such as a 2-tetrahydropyranyl group or a 1-methoxy-1-cyclohexyl group; an alkoxycarbonyl group, e.g., having 2 to 6 carbon atoms such as an ethoxycarbonyl group, a t-butoxycarbonyl group and a t-amyloxycarbonyl group; an aralkoxycarbonyl group, e.g., having 8 to 10 carbon atoms such as a benzyloxycarbonyl group, a p-methoxybenzyloxycarbonyl group, a p-ethoxybenzyloxycarbonyl group and a p-chlorobenzyloxycarbonyl group.

The reaction of hydrolysis of the epoxy group in the compound represented by the formula (II) can be carried out in a solvent such as 2-methoxyethanol, methanol, ethanol, dimethylformamide, dioxane, ethylene glycol, tetrahydrofuran, diethylene glycol, ethylene glycol dimethyl ether, diethyl glycol dimethyl ether and the like in the presence of a hydrolyzing catalyst such as sodium acetate, sodium benzoate and the like at a temperature of about 50° to about 200° C., preferably 70° C.

to 120° C., for about 1 to about 120 hours, preferably 12 to 72 hours.

The hydrolysis reaction can be carried out using the hydrolyzing catalyst in an amount of about 1 to about 10 mols, preferably 2 to 4 mols, per mol of the compound of the formula (II). The compound of the formula (II) can advantageously be used at a concentration of about 1 to about 30, preferably 5 to 10, % by weight in the solvent. Completion of the hydrolysis reaction can be monitored using thin layer chromatography using a solvent system of chloroform; ethanol (19:1 by volume).

After completion of the reaction, the solvent is evaporated from the reaction mixture, and the residue is dissolved in methanol, ethanol, pyridine and the like. The resulting solution is then subjected to an acetylation reaction using acetyl chloride or acetic anhydride to obtain crude 2-O-(3,4-di-O-acetyl-2,6-diethoxycarbonylamino-2,6-dideoxy-α-D-glucopyranosyl)-1L-1,6-di-O-acetyl-3,4,5-trideoxy-3,5-diethoxycarbonylamino-tyro-inositol.

The acetylation reaction can be carried out in a conventional manner using acetyl chloride or acetic anhydride, and is used to facilitate determination of the chemical structure of the product obtained.

The thus obtained crude product is dissolved in methanol, ethanol, acetone, 2-methoxyethanol, water and the like, and a base such as sodium hydroxide potassium hydroxide, barium hydroxide, hydrazine and the like is added to the solution thereby removing the protective groups for the hydroxyl group and the amino group. Acids can also be used for removal of the amino and hydroxyl group protective groups. However, bases are preferred and are particularly useful for industrial use. When bases as described above are used for removal of the protective groups, both protective groups for an amino group and a hydroxy group can be removed at the same time. The removal of the protective groups can be monitored using thin layer chromatography using a solvent system of 28% aqueous ammonia; n-butanol; ethanol; water (5:8:10:7 by volume) ($R_f$=0.25) to determine reaction completion.

This reaction to remove the protective groups can be conducted at a temperature of about 50° to about 150° C., preferably 70° C. to 120° C., for a period of about 1 to about 20 hours. After this reaction, where barium hydroxide, for example, is used for removal of the protective groups, carbon dioxide gas is introduced into the reaction mixture so as to precipitate the barium hydroxide and the precipitate is then removed. If necessary, the filtrate can be purified by column chromatography e.g., using Amberlite CG-50 (tradename produced by Rohm & Haas Co.) and the desired product is obtained.

The starting material of the process of this invention having the formula (II) can be prepared from neamine according to the reaction schematically shown in Reference Example 1 given hereinafter.

As described previously, the 5.6-epineamine of the present invention is also useful as an intermediate for producing other novel antibiotics.

The results of antimicrobial activity tests conducted on the 5,6-epineamine to demonstrate the unexpected effects obtained are shown in Table 1 below.

The inhibitory activities were determined at various concentrations of the compounds using the paper disc method against the various microorganisms indicated in Table 1 below and the numerical values show the inhibition zone diameter in terms of mm.

Table 1
Antimicrobial Activity of 5,6-Epineamine
(paper disc method; units indicate diameter (in mm) of the inhibition zone)

| Concentration (γ/ml) | B. subtilis ATCC 6633 | E. coli K-12 | S. aureus 6538P | S. epidermidis 12228 | Myco. tuberculosis 607 |
|---|---|---|---|---|---|
| 1000 | 33.9 | 31.5 | 26.2 | 25.7 | 24.4 |
| 500 | 29.8 | 28.3 | 23.5 | 21.0 | 18.6 |
| 250 | 26.5 | 25.8 | 20.0 | 29.0 | 11.0 |
| 125 | 23.4 | 23.3 | 16.5 | 16.1 | 0 |
| 62.5 | 21.2 | 21.1 | 12.7 | 14.0 | 0 |
| 31.2 | 19.2 | 19.7 | 0 | 10.8 | 0 |
| 15.6 | 17.5 | 16.2 | 0 | 0 | 0 |
| 7.8 | 14.8 | 12.8 | 0 | 0 | 0 |

As is apparent from the results shown in Table 1 above, the 5,6-epineamine of the present invention exhibits an excellent antimicrobial activity against various Gram positive and Gram negative microorganisms.

The starting compounds used in this invention are also novel substances, and the process for preparing such starting compounds is illustrated in Reference Example 1.

Further, the 5,6-epineamine of the present invention can be acetylated in an organic solvent such as methanol, ethanol, pyridine, etc. with acetic anhydride to obtain the corresponding N-acetylated compound. An example of the acetylation is given in Reference Example 2.

The present invention will now be illustrated in greater detail by way of an Example. Unless otherwise indicated, all parts, percents, ratios and the like are by weight.

Reference Example 1

Preparation of
6-O-(3,4-Di-O-acetyl-2,6-diethoxycarbonylamino-2,6-dideoxy-α-D-glucopyranosyl)-4,5-anhydro-1,2,3-trideoxy-1,3-diethoxycarbonylamino-epi-inositol 280 mg of 3',4',5-tri-O-acetyl-tetra-N-ethoxycarbonylneamine was dissolved in 2 ml of anhydrous pyridine, and 0.19 ml of methanesulfonyl chloride was added thereto under ice-cooling, followed by stirring at room temperature (about 20°-30° C.) overnight. The reaction was completed at the point when a spot of $R_f$ 0.33 disappeared and a spot of $R_f$ 0.68 was formed by thin layer chromatography using a mixed solvent of chloroform-ethanol (16:1 by volume). The reaction mixture was poured into 50 ml of ice-water, and immediately thereafter extracted twice with 10 ml portions of chloroform. The combined chloroform layer was washed successively with an aqueous sodium hydrogensulfate solution, an aqueous sodium hydrogencarbonate solution and water and then dried over anhydrous sodium sulfate. The solvent was evaporated, and the residue was recrystallized from ethanol to obtain 248 mg of 3',4',5-tri-O-acetyl-tetra-N-ethoxycarbonyl-6-O-methanesulfonylneamine in 92% yield.

Melting Point: 192°-193° C. $[\alpha]_D^{20}$: +59.3° (C 1.05, pyridine). NMR (CDCl$_3$): 1.26 (t, 12, J=7Hz, OCH$_2$CH$_3$), 1.99 (s, 3, OAc), 2.03 (s, 3, OAc), 2.07 (s, 3, OAc) and 3.02 (s, 3, SO$_2$CH$_3$).

Elemental Analysis for C$_{31}$H$_{50}$N$_4$O$_{19}$S: Calcd. (%): C, 45.69; H, 6.19; N, 6.88; S, 3.93. Found (%): C, 45.36; H, 6.01; N, 6.60; S, 4.11.

600 mg of 3',4',5-tri-O-acetyl-tetra-N-ethoxycarbonyl-6-O-methanesulfonylneamine was suspended in 6 ml of a 1N ethanolic sodium ethoxide followed by allowing the suspension to stand at room temperature overnight thereby obtaining a gelatinous substance. The substance was digested with ethanol, filtered, washed with ethanol and dried. The product was then acetylated in pyridine in a usual manner, and the resulting acetylated compound was dissolved in chloroform. The solution was passed through an alumina column, and the solvent evaporated. The residue was dissolved in benzene, and n-hexane was added to the solution thereby obtaining 218 mg of 6-O-(3,4-di-O-acetyl-2,6-diethoxycarbonylamino-2,6-dideoxy-α-D-glucopyranosyl)-4,5-anhydro-1,2,3-trideoxy-1,3-diethoxycarbonylamino-epi-inositol.

Melting Point: 116°–118° C.

$[\alpha]_D^{20}$: +126° (C, 1.05, pyridine).

NMR (CDCl$_3$) : δ 1.22 (t, 3, J=8Hz, OCH$_2$CH$_3$), 1.24 (t, 9, J=8Hz, 3OCH$_2$CH$_3$), 2.00 (s, 3, OAc) and 2.02 (s, 3, OAc).

Elemental Analysis for C$_{28}$H$_{44}$N$_4$O$_{15}$: Calcd. (%): C, 49.73; H, 6.55; N, 8.28. Found (%): C, 49.75; H, 6.45; ,N, 8.09.

Reference Example 2

46 mg of 5,6-epineamine was dissolved in 2 ml of methanol, and 0.05 ml of acetic anhydride was added to the solution. The mixture was allowed to stand overnight followed by concentration under reduced pressure, and the residue was washed with diethyl ether to obtain 58 mg of 1,3,2',6'-tetra-N-acetyl-5,6-epineamine in 83% yield.

Melting Point: higher than 250° C.

$[\alpha]_D^{20}$: +135° (C 2.0, H$_2$O).

NMR (D$_2$O): δ2.06 (s, 3H, NAc), 2.07 (s, 3H, NAc), 2.09 (s, 6H, 2xNAc) and 5.09 (d, 1H, J=3.5Hz, H-1').

Elemental Analysis for C$_{20}$H$_{34}$N$_4$O$_8$: Calcd. (1%): C, 48.09, H, 7.06, N, 11.22. Found (%): C, 48.16, H, 6.97, N, 11.15.

EXAMPLE (i) Preparation of 2-O-(3,4-Di-O-acetyl-2,6-diethoxycarbonylamino-2,6-dideoxy-α-D-glucopyranosyl)-1L-1,6-di-O-acetyl-3,4,5-trideoxy-3,5-diethoxycarbonylamino-tyroinositol 154 mg of 6-O-(3,4-di-O-acetyl-2,6-diethoxycarbonylamino-2,6-dideoxy-α-D-glucopyranosyl)-4,5-anhydro-1,2,3-trideoxy-1,3-diethoxycarbonylamino-epi-inositol, 60 mg of sodium acetate and 24 mg of ammonium chloride were dissolved in 5 ml of a 60% 2-methoxyethanol aqueous solution. The reaction mixture was heated while refluxing for 48 hours, and the solvent evaporated. The residue was acetylated in pyridine to obtain 206 mg of 2-O-(3,4-di-O-acetyl-2,6-diethoxycarbonylamino-2,6-dideoxy-α-D-glucopyranosyl)-1L-1,6-di-O-acetyl-3,4,5-trideoxy-3,5-diethoxycarbonylamino-tyro-inositol.

(ii) Preparation of 2-O-(2,6-Diamino-2,6-dideoxy-α-D-glucopyranosyl-1L-4-deoxy-tyro-inosadiamine (5,6-epineamine)

13.8 g of 2-O-(3,4-di-O-acetyl-2,6-diethoxycarbonylamino-2,6-dideoxy-α-D-glucopyranosyl)-1L-1,6-di-O-acetyl-3,4,5-trideoxy-3,5-diethoxycarbonylamino-tyro-inositol was dissolved in 6 ml of methanol, and a solution of 11 g of barium hydroxide in 35 ml of water was added to the solution. The resulting mixture was heated at 90° C. for 10 hours, and carbon dioxide gas was then bubbled into the reaction mixture. The precipitate was filtered, and the filtrate was dried under reduced pressure. Purification by column chromatography using an ion-exchange resin, Amberlite CG-50, gave 129 mg of 5,6-epineamine.

Melting Point: 110°–129° C. (with decomposition).

$[\alpha]_D^{20}$: +149° (C 1.2, H$_2$O).

While the invention has been described in detail and with reference to specific embodiments thereof, it will be apparent to one skilled in the art that various changes and modifications can be made therein without departing from the spirit and scope thereof.

What is claimed is:

1. 5,6-Epineamine represented by the formula (I)

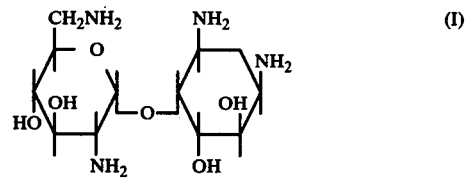

2. A compound represented by the formula

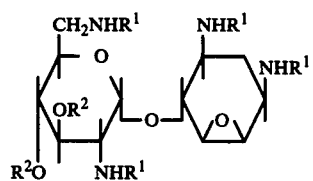

wherein wherein
R$^1$ represents a member selected from the group consisting of a methoxycarbonyl group, an ethoxycarbonyl group, an isopropoxycarbonyl group, a butoxycarbonyl group, a phenoxycarbonyl group, a p-nitrophenoxycarbonyl group, a benzyloxycarbonyl group, a p-methoxybenzyloxycarbonyl group, a p-ethoxybenzyloxycarbonyl group, a p-chlorobenzyloxycarbonyl group, and a p-nitrobenzyloxycarbonyl group and;

R$^2$ represents a member selected from the group consisting of an acetyl group, a propionyl group, a butyryl group, a benzoyl group, a p-chlorobenzoyl group, a p-nitrobenzoyl group, a 2-tetrahydropyranyl group, a 1-methoxy-1-cyclohexyl group, an ethoxycarbonyl group, a t-butoxycarbonyl group, a t-amyloxycarbonyl group, a benzyloxycarbonyl group, a p-methoxybenzyloxycarbonyl group, a p-ethoxybenzyloxycarbonyl group and a p-chlorobenzylcarbonyl group.

* * * * *